United States Patent
Burka et al.

(10) Patent No.: US 11,093,122 B1
(45) Date of Patent: Aug. 17, 2021

(54) GRAPHICAL USER INTERFACE FOR DISPLAYING CONTEXTUALLY RELEVANT DATA

(71) Applicant: Allscripts Software, LLC, Raleigh, NC (US)

(72) Inventors: Andrew Burka, Raleigh, NC (US); Ross C. Teague, Cary, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 76 days.

(21) Appl. No.: 16/202,994

(22) Filed: Nov. 28, 2018

(51) Int. Cl.
 *G06F 3/0484* (2013.01)
 *G06F 3/0488* (2013.01)
 *G16H 10/60* (2018.01)

(52) U.S. Cl.
 CPC ........ *G06F 3/04842* (2013.01); *G06F 3/0488* (2013.01); *G16H 10/60* (2018.01)

(58) Field of Classification Search
 CPC .... G06F 3/04842; G06F 3/0488; G16H 10/60
 See application file for complete search history.

(56) References Cited

U.S. PATENT DOCUMENTS

| | | | |
|---|---|---|---|
| 5,611,031 A | 3/1997 | Hertzfeld et al. | |
| 6,523,022 B1 | 2/2003 | Hobbs | |
| 6,948,126 B2 * | 9/2005 | Malamud | G06F 3/04812 715/715 |
| 7,603,341 B2 | 10/2009 | Martin et al. | |
| 7,650,575 B2 | 1/2010 | Cummins et al. | |
| 7,823,054 B2 | 10/2010 | Forstall et al. | |
| 8,416,266 B2 * | 4/2013 | Shoemaker | G06F 3/0481 345/471 |
| 2002/0184402 A1 * | 12/2002 | Gangopadhyay | G06F 9/451 719/315 |
| 2006/0265417 A1 | 11/2006 | Amato et al. | |
| 2007/0118400 A1 * | 5/2007 | Morita | G16H 40/63 705/2 |
| 2010/0122194 A1 * | 5/2010 | Rogers | G06F 3/0482 715/769 |
| 2010/0174986 A1 | 7/2010 | Lee et al. | |
| 2012/0030567 A1 * | 2/2012 | Victor | G06F 3/0486 715/702 |
| 2012/0086662 A1 * | 4/2012 | Ashikawa | G06F 3/04883 345/173 |
| 2013/0047104 A1 * | 2/2013 | Chen | G06F 3/0482 715/765 |

(Continued)

*Primary Examiner* — Yongjia Pan
(74) *Attorney, Agent, or Firm* — Medley, Behrens & Lewis, LLC

(57) ABSTRACT

An improved graphical user interface (GUI) is disclosed herein. A computing device displays the GUI on a display. The GUI comprises a data element. The computing device receives a first indication that the data element has been selected within the GUI by a selection article. As the data element remains selected, the computing device receives a second indication that the selection article has been moved in a direction. As the data element remains selected, the computing device displays contextual data for the data element on the display. The contextual data displayed may be based upon the direction in which the selection article was moved. Responsive to receiving a third indication that the data element fails to remain selected by the selection article, the computing device removes the contextual data from the GUI.

20 Claims, 15 Drawing Sheets

(56) References Cited

U.S. PATENT DOCUMENTS

| | | | |
|---|---|---|---|
| 2014/0267130 A1* | 9/2014 | Hwang | G06F 3/0488 345/174 |
| 2014/0380158 A1* | 12/2014 | Kapahi | G06F 3/0481 715/711 |
| 2014/0380226 A1* | 12/2014 | Okigami | G06F 3/04883 715/776 |
| 2015/0066643 A1* | 3/2015 | Choi | G06Q 30/0255 705/14.53 |
| 2015/0106737 A1* | 4/2015 | Montoy-Wilson | G06F 9/451 715/745 |
| 2015/0248494 A1* | 9/2015 | Mital | G06F 16/90328 707/722 |
| 2018/0164963 A1* | 6/2018 | Ku | G06F 3/0483 |
| 2018/0292978 A1* | 10/2018 | Davies | G06F 3/04845 |

* cited by examiner

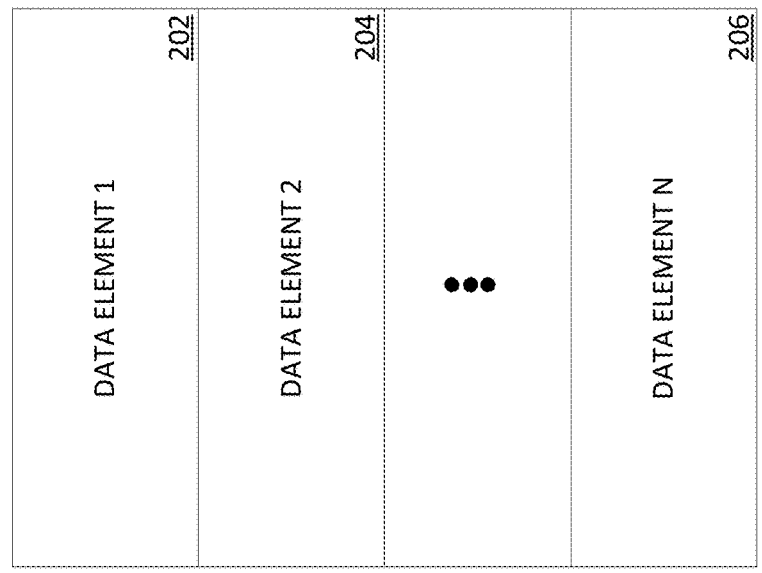

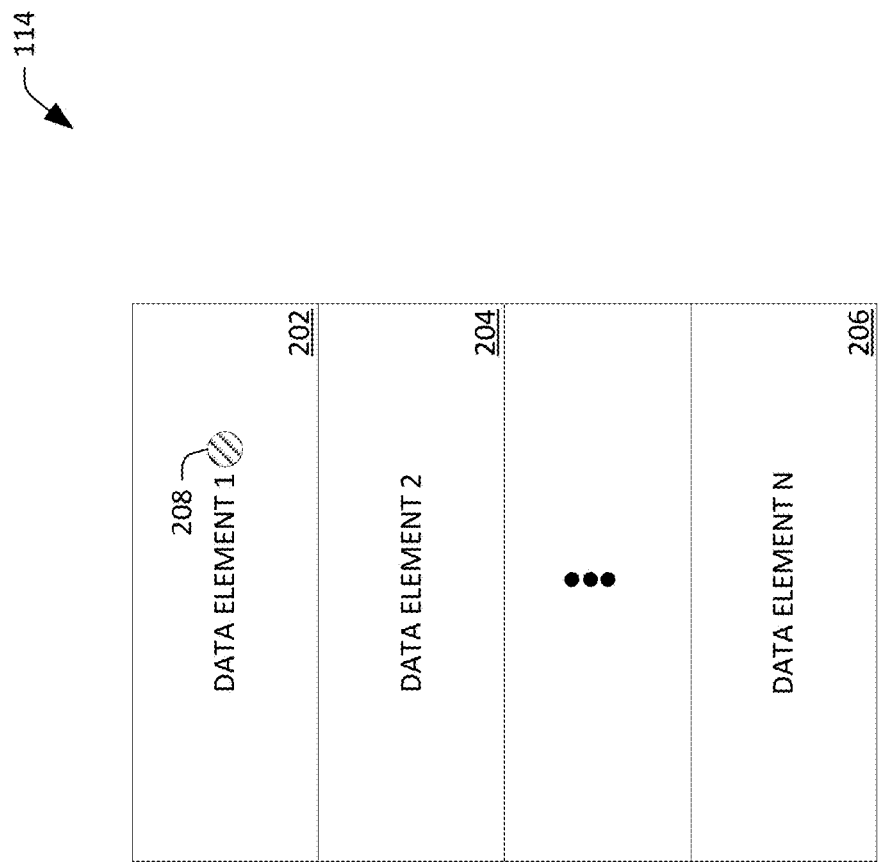

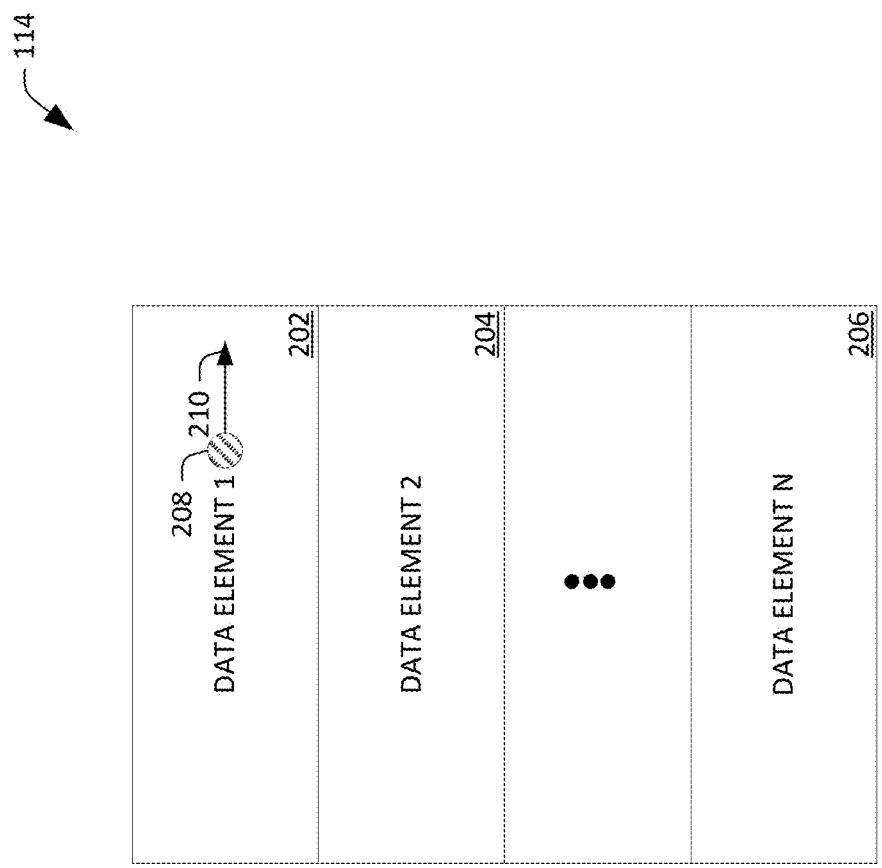

FIG. 5A

| BRIGGS, Lily \| DOB: 12-May-1946 \| Female | |
|---|---|
| Snapshot | |
| Outside Room Activities | OUTSIDE ROOM ACTIVITIES |
| Patient Checklist | Relevant Vitals to Collect Outside of Exam Room: |
| RFV -- Shortness of Breath | Height (Today)  6'6" |
| Review Vitals | Weight (Today)  200 lbs |
| Review Allergies | |
| Review Medications | Relevant Orders: |
| Review History | Urinalysis (10-18-2018) |
| Review and Send | |

| BRIGGS, Lily \| DOB: 12-May-1946 \| Female | |
|---|---|
| Snapshot | OUTSIDE ROOM ACTIVITIES |
| Outside Room Activities | Relevant Vitals to Collect Outside of Exam Room: |
| Patient Checklist | |
| RFV -- Shortness of Breath | Height (Today)  6'6" |
| Review Vitals | 504 |
| Review Allergies | Weight (Today)  200 lbs |
| Review Medications | Relevant Orders: |
| Review History | Urinalysis (10-18-2018) |
| Review and Send | |

| BRIGGS, Lily \| DOB: 12-May-1946 \| Female | | |
|---|---|---|
| Snapshot | | |
| Outside Room Activities | OUTSIDE ROOM ACTIVITIES | |
| Patient Checklist | Relevant Vitals to Collect Outside of Exam Room: | |
| RFV -- Shortness of Breath | | |
| Review Vitals | Height (Today) | 6'6" |
| Review Allergies | Weight (Today) | 200 lb |
| Review Medications | | |
| Review History | Relevant Orders: | |
| Review and Send | Urinalysis (10-18-2018) | |

BRIGGS, Lily | DOB: 12-May-1946 | Female

| Snapshot | WEIGHT TRENDS | OUTSIDE ROOM ACTIVITIES |
|---|---|---|
| Outside Room Activities | | Relevant Vitals to Collect Outsid |
| Patient Checklist | Past Values | |
| RFV -- Shortness of Breath | | Height (Today) — 506 |
| Review Vitals | | 504 — Weight (Today) |
| Review Allergies | | |
| Review Medications | 09-Mar-2017 | Relevant Orders: |
| Review History | 175 lbs | Urinalysis (10-18-2018) |
| Review and Send | 22-Dec-2016 | |
| | 175 lbs | 502 |
| | 508 | |

| BRIGGS, Lily \| DOB: 12-May-1946 \| Female | | OUTSID |
|---|---|---|
| Snapshot | | |
| Outside Room Activities | WEIGHT TRENDS | Relevant |
| Patient Checklist | Past Values | Height (T — 504 — 506 |
| RFV -- Shortness of Breath | | |
| Review Vitals | | |
| Review Allergies | | Relevant |
| Review Medications | 09-Mar-2017  221 / 225 lbs / 175 | Urinalysis |
| Review History | | |
| Review and Send | 22-Dec-2016  218 / 225 lbs / 175 | |
| | 508 | 502 |

GRAPHICAL USER INTERFACE FOR DISPLAYING CONTEXTUALLY RELEVANT DATA

BACKGROUND

A graphical user interface (GUI) may display one or more (visual) data elements on a display of a computing device. As the display has a limited area in which to display the one or more data elements, displaying contextual data for the one or more data elements in a space-efficient manner can be challenging.

In an explicit navigation approach for displaying contextual data for a data element, a GUI can receive input causing the GUI to display the contextual data separately (e.g., in a different window) from the data element. When display of the contextual data is no longer required, the GUI receives explicit input from the user causing the GUI to navigate back to the data element.

In a progressive disclosure approach for displaying contextual data for a data element, a GUI can receive a selection of the data element causing the GUI to display identifiers for different contextual data for the data element. The GUI may then receive a selection of an identifier for contextual data in the identifiers for the different contextual data and the GUI may be updated to display the contextual data for the data element alongside or as an overlay to the data element. When display of the contextual data is no longer required, the GUI can receive an explicit close command (e.g., clicking on a close button) causing the contextual data to be removed from the GUI.

In a hover approach for displaying contextual data for a data element, a GUI can receive input causing a selection of the data element (e.g., placing a mouse cursor of a mouse over the data element such that the cursor "hovers" over the data element). When the data element remains selected for a certain duration of time (e.g., a few seconds), the GUI can be updated to display the contextual data for the data element. For instance, the contextual data can be displayed as a caption to the data element. When the data element becomes unselected (e.g., the mouse cursor is moved away from the data element), the contextual data may be removed from the GUI.

The above-described computer-implemented techniques for displaying contextual data for a data element in a GUI suffer from various deficiencies. First, the explicit navigation approach and the progressive disclosure approach require a significant amount of user input in order for the GUI to display the contextual data. This leads to an inefficient use of computing resources. Second, the hover approach is not well-suited for touchscreen displays that are common on mobile computing devices. More specifically, when implemented on a touchscreen of a mobile computing device, the hover approach requires a user to place and hold a digit (e.g., a finger or a thumb) of the user on the data element shown on the touchscreen in order to trigger display of the contextual data. However, the "place and hold" input gesture tends to be reserved (i.e., already assigned to a specific command) by an operating system of the mobile computing device. Hence, it may be difficult or impossible to implement the hover approach in mobile computing devices having touchscreen displays.

SUMMARY

The following is a brief summary of subject matter that is described in greater detail herein. This summary is not intended to be limiting as to the scope of the claims.

Described herein are various technologies pertaining to an improved graphical user interface (GUI) for displaying contextual data for a data element. The GUI may display the contextual data based upon a direction in which a selection article (e.g., a mouse or a digit (e.g., a finger or a thumb) of a user) that selects the data element is moved. In an embodiment, an electronic health records application (EHR) may display the GUI on a display of a computing device in order to display clinical data for patients and contextual data for the clinical data.

In operation, a computing device operated by a user displays a GUI on a display of the computing device. The GUI comprises a data element. The computing device receives a first indication that the data element has been selected (e.g., a depression of a mouse button of a mouse while a cursor of the mouse is placed on the data element, placing a digit of a user on a touchscreen display at a location where the data element is displayed, etc.) within the GUI by a selection article. As the data element remains selected within the GUI by the selection article (e.g., as the mouse button of the mouse remains depressed, as the digit of the user remains placed on the touchscreen display, etc.), the computing device receives a second indication that the selection article has been moved in a direction (e.g., the mouse is moved in the direction while the mouse button remains depressed, the digit of the user is moved in the direction on the touchscreen display, etc.).

The computing device accesses contextual data for the data element based upon the data element. In an embodiment where the contextual data is stored in memory or a data store of the computing device, the computing device accesses the contextual data from the memory or the data store. In an embodiment where the contextual data is stored on a server computing device, the computing device transmits an identifier for the data element to the server computing device. The server computing device retrieves the contextual data based upon the identifier for the data element and transmits the contextual data for the data element to the computing device.

As the data element remains selected within the GUI by the selection article, the computing device displays the contextual data for the data element within the GUI. At least a portion of the data element is displayed concurrently with the contextual data within the GUI. Responsive to receiving a third indication that the data element fails to remain selected within the GUI by the selection article (e.g., the mouse button was released, a digit of the user was removed from a touchscreen of the computing device, etc.), the computing device removes the contextual data from the GUI while continuing to display the data element.

In an embodiment, the contextual data displayed may be based upon the direction in which the selection article was moved. In an example, when the selection article is moved in a first direction, the contextual data may be past values for the data element or a past version of the data element. In another example, when the selection article is moved in a second direction, the contextual data may be projected future values for the data element or a projected future version of the data element.

The above-described technologies present various advantages over conventional GUIs. First, the above-described technologies are selection article agnostic and hence may be utilized across computing devices that utilize different selection articles (e.g., a mouse for a traditional desktop computing device, a digit of a user for a mobile computing device including a touchscreen, etc.). Second, the above-described technologies require less input to display contextual data than conventional GUIs, and thus save computing resources. Third, the above-described technologies enable increased display of data as the contextual data is not bound to any existing elements within the GUI (unlike, for example, the hover approach described above). Fourth, unlike the hover approach, the above-described technologies do not interfere with input gestures reserved by operating systems of mobile computing devices including touchscreens.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIGS. 2A-2D depict sequential views of a graphical user interface (GUI) for displaying contextual data for a data element.

FIGS. 5A-5E depict sequential views of a GUI for displaying contextual data for a data element.

DETAILED DESCRIPTION

Figure 1:
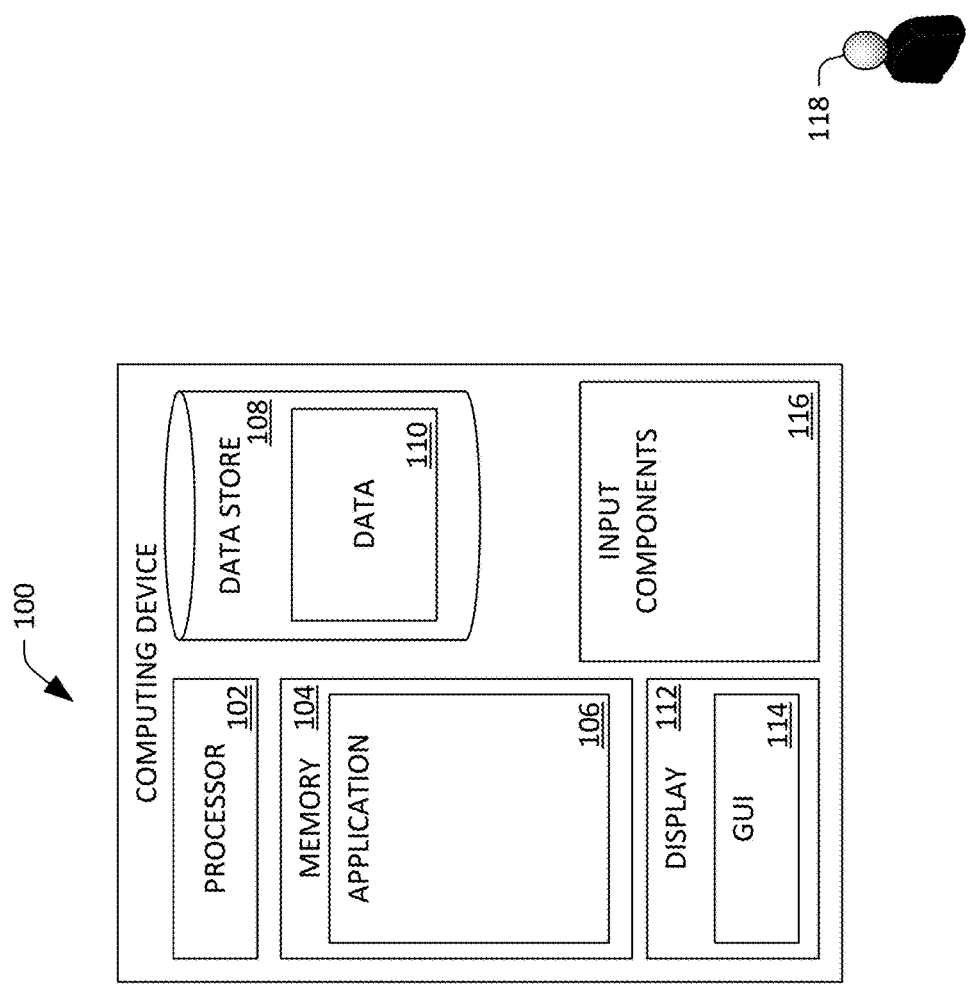
FIG. 1 is a functional block diagram of an exemplary computing device.

Various technologies pertaining to displaying contextual data for a data element within a graphical user interface (GUI) are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing device 100 that facilitates displaying contextual data for a data element on a display is illustrated. The computing device 100 is operated by a user 118. In a non-limiting example, the computing device 100 may be a desktop computing device, a laptop computing device, a tablet computing device, a smartphone, or a wearable computing device such as a smartwatch. The computing device 100 includes a processor 102 and memory 104, wherein the memory 104 has an application 106 loaded therein. The application 106 (when executed the processor 102) is configured to access and display data elements as well as contextual data for the data elements.

The computing device 100 may comprise a data store 108. The data store 108 may comprise data 110 (e.g., data elements, contextual data for data elements, etc.).

The computing device 100 comprises a display 112, whereupon a GUI 114 (described in greater detail below) is presented thereon. The GUI 114 is configured to display contextual data for a data element. In an embodiment, the display 112 may be a touchscreen. The computing device 100 further comprises input components 116 suitable for data input. In a non-limiting example, the input components 116 may include a mouse, a keyboard, a touchscreen, a stylus, a trackpad, a scroll wheel, a camera, and/or a video camera.

FIGS. 2A-2D depict operation of the computing device 100. More specifically, FIGS. 2A-2D depict sequential views of the GUI 114. The GUI 114 may be presented on the display 112 of the computing device 100 described above. Moreover, the GUI 114 may be part of the application 106.

Turning now to FIG. 2A, the GUI 114 comprises a plurality of data elements 202-206 (e.g., a first data element 202, a second data element 204, an Nth data element 206). In an example, the plurality of data elements 202-206 may be text displayed on the display 112. In another example, the plurality of data elements 202-206 may be images displayed on the display 112.

In an embodiment, a data element in the plurality of data elements 202-206 (e.g., the first data element 202) may be highlighted within the GUI 114 to indicate that contextual data for the first data element 202 is available.

With reference now to FIG. 2B, the GUI 114 receives a selection 208 of the first data element 202 by a selection article, thereby causing the computing device 100 to receive a first indication that the GUI 114 has received the selection 208 of the first data element 202. The selection article is an object that is capable of providing input to the computing device 100 via the GUI 114. For instance, the selection article may be a mouse, a trackpad, a stylus, a digit (e.g., a finger or a thumb) of the user 118, etc. In an example, when the selection article is a mouse, the selection 208 may be caused by a depression of a mouse button (without a release of the mouse button) on the mouse while a cursor of the mouse is located on the first data element 202 displayed on the GUI 114. In another example, when the selection article is a digit of the user 118 and the display 112 is a touchscreen, the selection 208 may be caused by a placement of the digit of the user 118 on an area of the GUI 114 that is currently displaying the first data element 202.

Referring now to FIG. 2C, as the first data element 202 remains selected within the GUI 114 by the selection article, the selection article is moved in a direction 210, thereby causing the computing device 100 to receive a second indication that the selection article has been moved in the direction 210. In an example, when the selection article is a mouse, the mouse may be moved by the user 118 in the direction 210 while a mouse button on the mouse remains depressed (i.e. dragging the mouse in the direction 210 as the mouse button remains depressed). In another example, when the selection article is a digit of the user 118 and the display 112 is a touchscreen, the user 118 may move the digit on the display 112 in the direction 210.

Figure 2D:
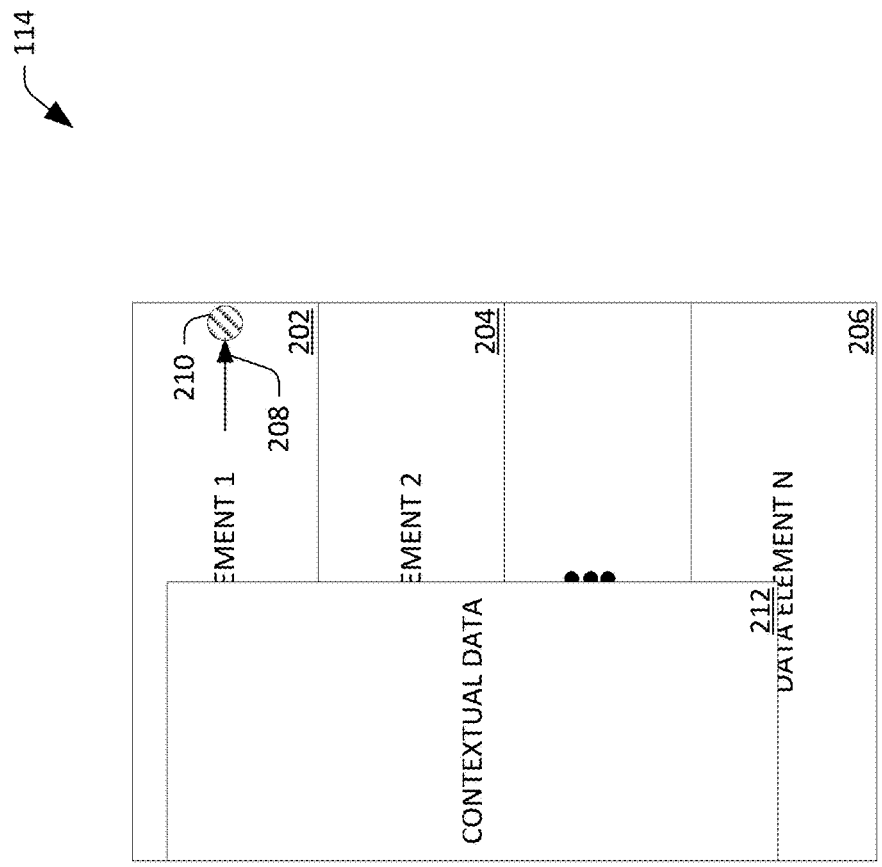

Turning now to FIG. 2D, as the first data element 202 remains selected within the GUI 114 by the selection article, the computing device 100 updates the GUI 114 to display contextual data 212 for the first data element 202. As shown in FIG. 2D, at least a portion of the first data element 202 remains displayed concurrently with the contextual data 212.

In order to display the contextual data 212, the computing device 100 accesses the contextual data 212 for the first data element 202. In an embodiment where the contextual data 212 for the first data element 202 has already been received and is stored in the memory 104 and/or the data store 108, the computing device 100 may access the contextual data 212 for the first data element 202 from the memory 104 and/or the data store 108. In another embodiment, responsive to receiving the second indication, the computing device 100 may transmit an identifier for the first data element 202 to another computing device (e.g., a server computing device) that is in communication with the computing device 100 via a network (e.g., the Internet, intranet, etc.). Responsive to receiving the identifier for the first data element 202, the server computing device may retrieve the contextual data 212 for the first data element 202 by executing a search over a data store based upon the identifier for the first data element 202. The data store may store data elements as well as contextual data for the data elements. The search produces search results including the contextual data 212 for the first data element 202. The server computing device may then transmit the contextual data 212 for the first data element 202 to the computing device 100.

In an embodiment, the computing device 100 selects the contextual data 212 for the first data element 202 from amongst a plurality of contextual data for the first data element 202. In the embodiment, selecting the contextual data 212 may be based upon the direction 210 in which the selection article is moved (described in greater detail below). For example, the contextual data 212 for the first data element 202 may be selected (and displayed) when the selection article is moved in the direction 210 and second contextual data for the first data element 202 may be selected (and displayed) when the selection article is moved in a second direction (not shown) that is different from the direction 210.

In an embodiment, the first indication is received by the computing device 100 at a first time and the second indication is received by the computing device 100 at a second time. In the embodiment, the computing device access and displays the contextual data 212 when the first time and the second time are within a threshold time range (e.g., 1 to 3 seconds). When the first time and the second time are outside of the threshold time range, the computing device 100 may fail to access and display the contextual data 212 for the first data element 202.

In an embodiment, the selection article may be moved in the direction 210 to a threshold distance. When the selection article is moved at or beyond the threshold distance, the computing device 100 displays the contextual data 212 within the GUI 114. When the selection article fails to be moved to the threshold distance, the computing device 100 fails to display the contextual data 212 within the GUI 114.

Subsequently, the first data element 202 may fail to remain selected within the GUI 114 by the selection article. In an example, when the selection article is a mouse and the selection 208 is accomplished via a depression of a mouse button of the mouse, the user 118 may release the (depressed) mouse button. In another example, when the selection article is a digit of the user 118 and the display 112 is a touchscreen, the user 118 may remove the digit from the display 112. As a result of the first data element 202 failing to remain selected within the GUI 114 by the selection article, the computing device 100 receives a third indication that the first data element 202 fails to remain selected within the GUI 114 by the selection article. Responsive to receiving the third indication, the computing device 100 removes the contextual data 212 from the GUI 114. The first data element 202 (as well as the other data elements 204-206) remain displayed within the GUI 114. Thus, when the first data element 202 fails to remain selected within the GUI 114 by the selection article, the computing device 100 causes the GUI 114 to return to the state shown in FIG. 2A.

In an embodiment, the computing device 100 may receive an indication that the selection article has been moved to a threshold point in the direction 208. Responsive to receiving the third indication that the first data element 202 fails to remain selected within the GUI 114 by the selection article, the computing device 100 anchors the contextual data 212 within the GUI 114 such that the contextual data 212 continues to be displayed within the GUI 114.

In an embodiment, the computing device 100 presents the contextual data 212 for the first data element 202 in a pane within the GUI 114. The pane is presented as an overlay to the first data element 202. The pane may comprise a first portion and a second portion. As the selection article is moved in the direction 210 to a first point in the direction 210, the computing device 100 displays the first portion of the pane within the GUI 114. As the selection article is moved in the direction 210 to a second point in the direction 210, the computing device 100 displays both the first portion of the pane and the second portion of the pane within the GUI 114. Thus, as the selection article is moved to a greater distance in the direction, the computing device 100 updates the GUI 114 to display an increasing portion of the pane. Moreover, a transition from display of neither the first portion nor the second portion to display of the first portion and a transition from display of the first portion to display of both the first portion and the second portion may be a continuous animation. In the embodiment, removal of the contextual data 212 from the GUI 114 is also a continuous animation. Although the above-described embodiment has been described as utilizing a pane having a first portion and a second portion, it is to be understood that the pane may have more than two portions.

Figure 3:
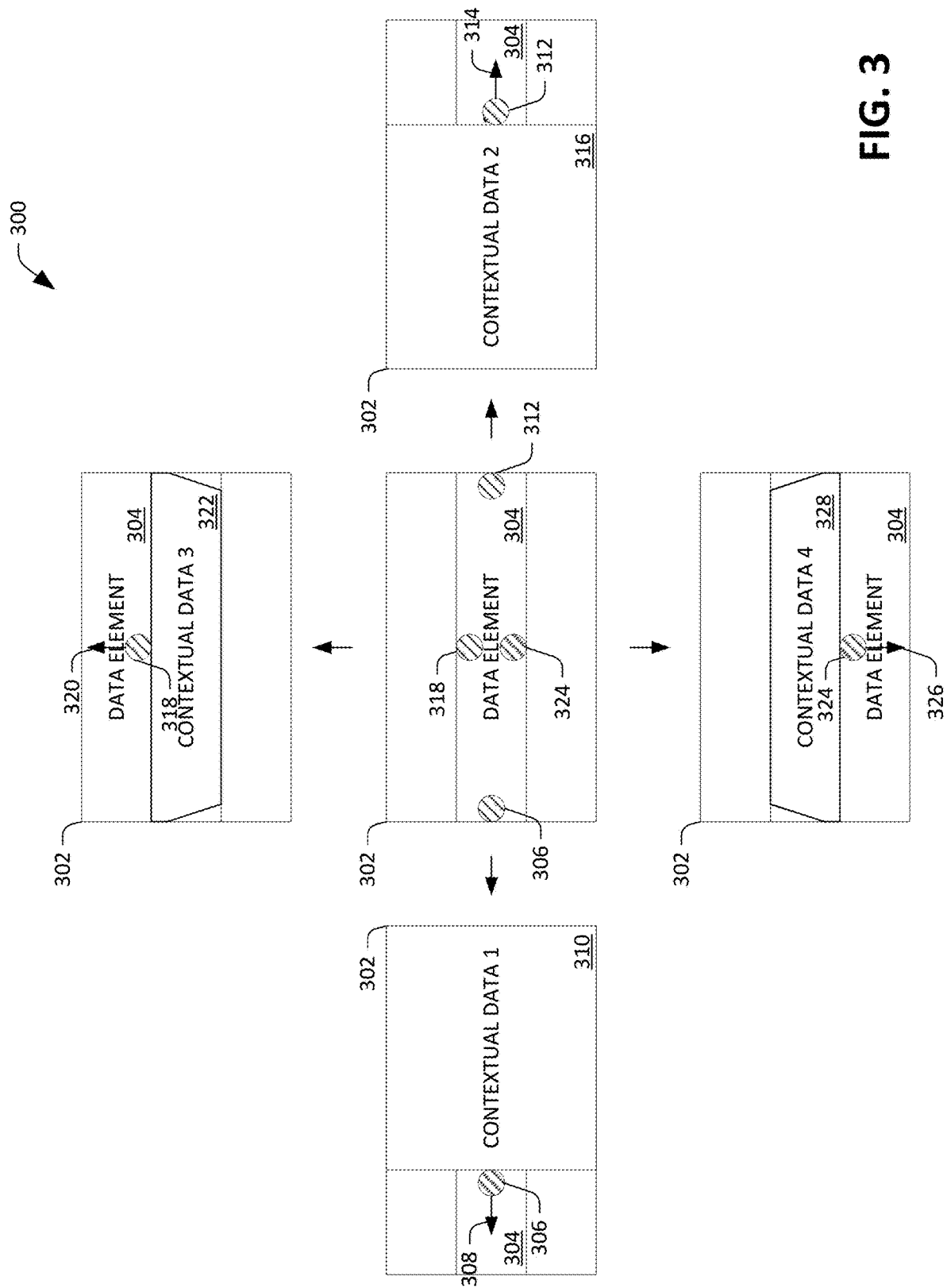
FIG. 3 depicts displaying contextual data for a data element within a GUI based upon a direction in which a selection article is moved.

Referring now to FIG. 3, an illustration 300 of different contextual data being displayed based upon a direction in which a selection article is moved is depicted. As shown in FIG. 3, a GUI 302 comprises a data element 304. The GUI 302 may also comprise other data elements (not shown). In an example, the GUI 302 may be or include the GUI 114 and/or the GUI 114 may be or include the GUI 302. Thus, the GUI 302 may be displayed on the display 112 of the computing device 100.

When the GUI 302 receives a selection 306 of the data element 304 by way of the selection article and the selection article is moved in the first direction 308, the computing device 100 may update the GUI 302 to display first contextual data 310 for the data element 304. In a non-limiting example, the first contextual data 310 may be projected future values or suggestions for the data element 304.

When the GUI 302 receives a selection 312 of the data element 304 by way of the selection article and the selection article is moved in a second direction 314, the computing device 100 may update the GUI 302 to display second contextual data 316 for the data element 304. In a non-limiting example, the second contextual data 316 may past values or suggestions for the data element 304.

When the GUI 302 receives a selection 318 of the data element 304 by way of the selection article and the selection article is moved in a third direction 320, the computing device 100 may update the GUI 302 to display third contextual data 322 for the data element 304. In a non-limiting example, the third contextual data 322 may be related data of the data element 304.

When the GUI 302 receives a selection 324 of the data element 304 by way of the selection article and the selection article is moved in a fourth direction 326, the GUI 302 may be updated to display fourth contextual data 328 for the data element 304. In a non-limiting example, the fourth contextual data 328 may include identifiers for users that last modified the data element 304.

Although FIG. 3 displays movement of the selection article in four different directions, it is to be understood that different contextual data for the data element 304 may be selected and displayed based upon movement of the selection article in many different directions (e.g., eight different directions). Additionally, although FIG. 3 depicts the selections 306, 312, 318, and 324 as being in particular locations on the data element 304 displayed in the GUI 302, it is to be understood that in an embodiment, the selections 306, 312, 318, and 324 may be made at any location on the data element 304 displayed in the GUI 302.

Figure 4:
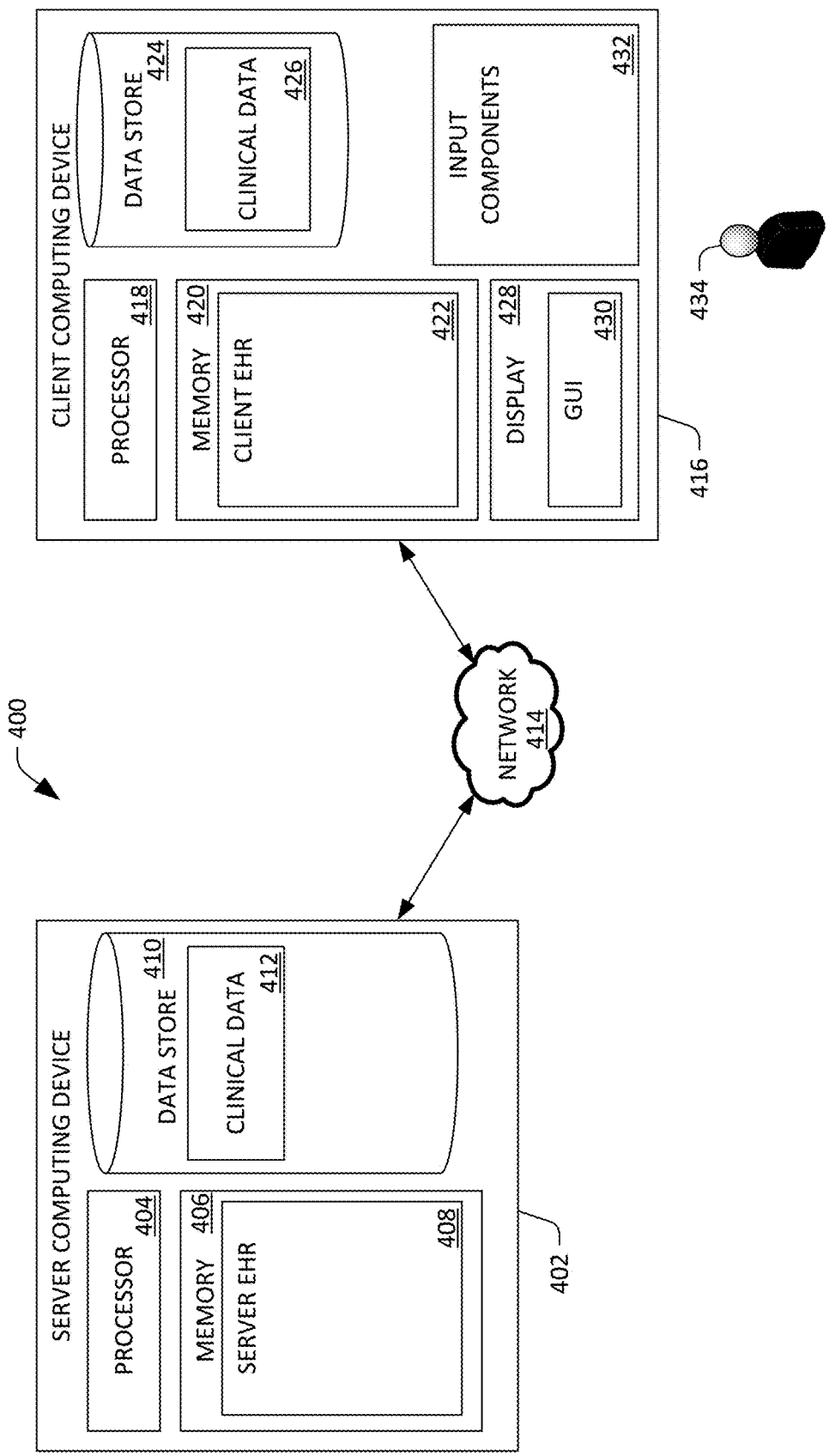
FIG. 4 is a functional block diagram of an exemplary computing system that facilitates displaying contextual data for a data element within a GUI.

Turning now to FIG. 4, an exemplary computing system 400 that facilitates displaying contextually relevant clinical data for a patient is illustrated. The computing system 400 includes a server computing device 402. The server computing device 402 comprises a processor 404 and memory 406, wherein the memory 406 has a server electronic health records application (server EHR) 408 loaded therein. In general, the server EHR 408 (when executed by the processor 404) is configured to perform a variety of tasks related to patient healthcare in a healthcare facility (e.g., patient intake, prescription generation, patient record creation and maintenance, etc.).

The server computing device 402 may additionally comprise a data store 410. The data store 410 includes clinical data 412 for patients (amongst other data), wherein the clinical data 412 is maintained by the server EHR 408. The clinical data 412 may include electronic health records, prescription records, claims data, patient/disease registries, health surveys data, and/or clinical trials data.

The computing system 400 additionally includes a client computing device 416 that is in communication with the server computing device 402 by way of a network 414 (e.g., the Internet, intranet, etc.). The client computing device 416 is operated by a healthcare worker 434 (e.g., a clinician). In a non-limiting example, the client computing device 416 may be a desktop computing device, a laptop computing device, a tablet computing device, a smartphone, or a wearable computing device such as a smartwatch.

The client computing device 416 comprises a processor 418 and memory 420, wherein the memory 420 has a client electronic health records application (client EHR) 422 loaded therein. In general, the client EHR 422 (when executed by the processor 418) is configured to interface with the server EHR 408 executing on the server computing device 402, thereby providing the healthcare worker 434 with access to functionality of the server EHR 408.

The client computing device 416 may include a data store 424. The data store 424 may comprise clinical data 426 for patients. It is understood that the clinical data 426 may overlap in part or wholly with the clinical data 412 retained in the data store 410 of the server computing device 402.

The client computing device 416 comprises a display 428, whereupon a GUI 430 for the client EHR 422 may be presented thereon. In an embodiment, the display 428 may be a touchscreen. The client computing device 416 further comprises input components 432 suitable for data input. In a non-limiting example, the input components 432 may include a mouse, a keyboard, a touchscreen, a stylus, a trackpad, a scroll wheel, a camera, and/or a video camera.

FIGS. 5A-5E depict exemplary operation of the computing system 400. More specifically, FIGS. 5A-5E depict sequential views of the GUI 430 for the client EHR 422. It is contemplated that the healthcare worker 434 wishes to view clinical data for a patient. As such, the client computing device 416 may receive access credentials of the healthcare worker 434 and may transmit the access credentials to the server EHR 408 executing on the server computing device 402. The server EHR 408 may authenticate the healthcare worker 434 based upon the access credentials and may provide the healthcare worker 434 with access to functionality of the server EHR 408 via the client EHR 422.

The client EHR 422 may receive an identifier for a patient as input from the healthcare worker 434. The client EHR 422 may then transmit the identifier for the patient to the server EHR 408. Responsive to receiving the identifier for the patient, the server EHR 408 may execute a search over the clinical data 412 based upon the identifier for the patient. The search produces search results including clinical data for the patient. The server EHR 408 then transmits the clinical data for the patient to the client EHR 422.

Turning now to FIG. 5A, responsive to receiving the clinical data for the patient, the client EHR 422 presents the GUI 430 on the display 428 of the client computing device 416. As shown in FIG. 5A, the GUI 430 displays various (clinical) data elements for the patient. For instance, the GUI 430 includes a name of the patient, a date of birth of the patient, a sex of the patient, a height of the patient, a weight of the patient, etc. Notably, the client EHR 422 displays some of the clinical data elements within a first pane 502 (e.g., the height of the patient, the weight of the patient, relevant orders of the patient, etc.) shown on the GUI 430.

With reference now to FIG. 5B, the client EHR 422 receives a first indication that a selection 504 of the weight of the patient displayed in the GUI 430 has been made by a selection article (similar to the process described above in the description of the operation of the computing device 100).

Referring now to FIG. 5C, as the weight of the patient remains selected within the GUI 430 by the selection article, the client EHR 422 receives a second indication that the selection article has been moved in a direction 506. Responsive to receiving the second indication, the client EHR 422 accesses contextual data for the weight of the patient and begins to display a portion of a second pane 508 shown on the GUI 430. When fully displayed, the second pane 508 will display contextual data for the weight of the patient. As a result of beginning to display the second pane 508, the client EHR 422 displays a smaller portion of the first pane 502.

Turning now to FIG. 5D, as the weight of the patient remains selected within the GUI 430 by the selection article and as the selection article continues to be moved in the direction 506, the client EHR 422 displays a greater portion of the second pane 508 and a smaller portion of the first pane 502 as compared to FIG. 5C.

Turning now to FIG. 5E, as the weight of the patient remains selected within the GUI 430 by the selection article and as the selection article is moved to a threshold distance in the direction 506, the client EHR 422 (fully) displays the contextual data for the weight of the patient in the second pane 508. For instance, as shown in FIG. 5E, the second pane 508 fully displays a line graph of past weight values for the patient, as well as past values of the weight of the patient (221 pounds on Mar. 9, 2017 and 218 pounds on Dec. 22, 2016) at healthcare appointments of the patient.

When the client EHR 422 receives a third indication that the weight of the patient fails to remain selected within the GUI 430 by the selection article, the client EHR 422 may cause the GUI 430 to revert to the state shown in FIG. 5A. As such, the second pane 508 may be removed from the GUI 430 while the entirety of the first pane 502 is displayed as in FIG. 5A. In an embodiment, the client EHR 422 may animate reverting the GUI 430 to the state shown in FIG. 5A.

Figure 6:
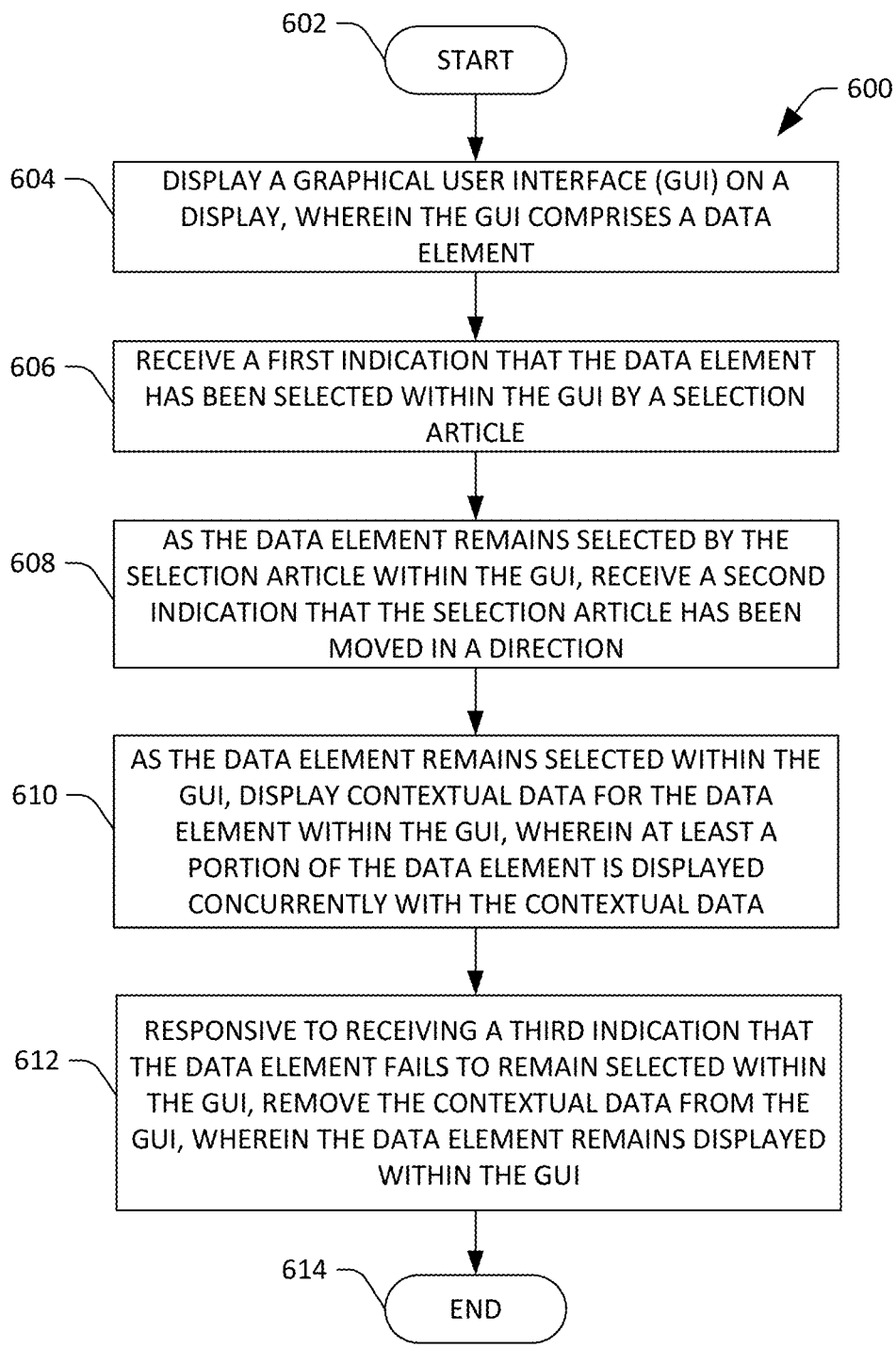
FIG. 6 is a flow diagram that illustrates an exemplary methodology performed by a computing device for displaying contextual data for a data element.
Figure 7:
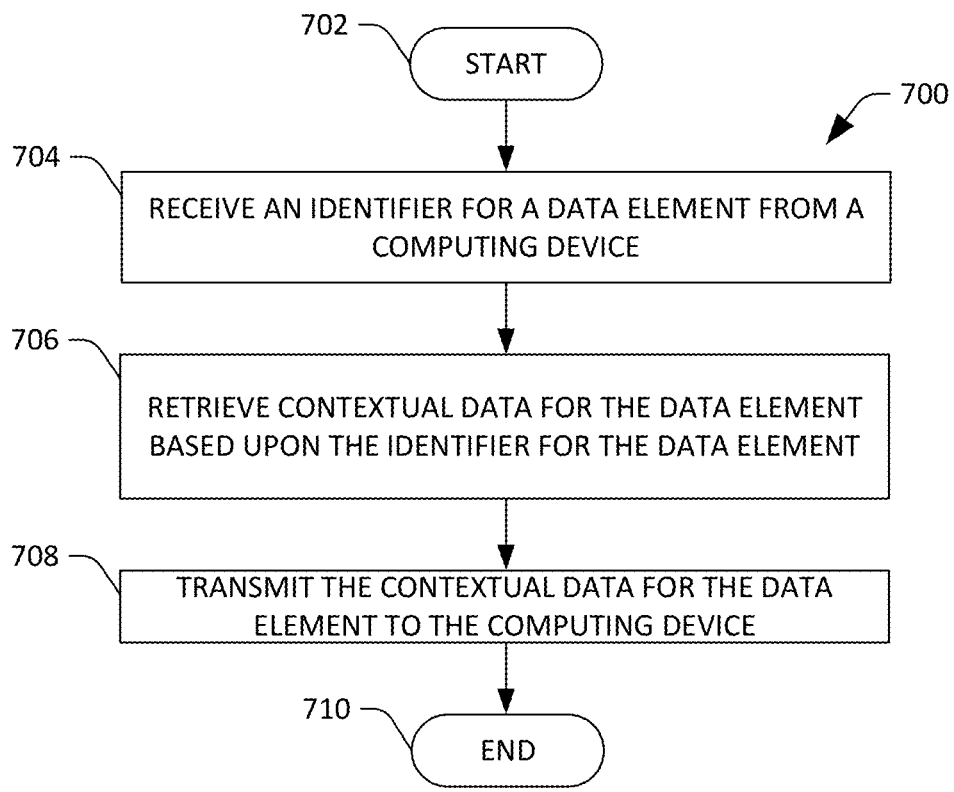
FIG. 7 is a flow diagram that illustrates an exemplary methodology performed by a server computing device that facilitates displaying contextual data for a data element.

FIGS. 6 and 7 illustrate exemplary methodologies relating to displaying contextual data for a data element within a GUI. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology 600 executed by a computing device that facilitates displaying contextual data for a data element is illustrated. The methodology 600 begins at 602, and at 604 the computing device displays a GUI on a display of the computing device. The GUI comprises a data element. At 606, the computing devices receives a first indication that the data element has been selected within the GUI by a selection article. At 608, as the data element remains selected within the GUI by the selection article, the computing device receives a second indication that the selection article has been moved in a direction. At 610, as the data element remains selected within the GUI by the selection article, the computing device displays contextual data for the data element within the GUI. At least a portion of the data element is displayed concurrently with the contextual data for the data element within the GUI. At 612, responsive to receiving a third indication that the data element fails to remain selected within the GUI by the selection article, the computing device removes the contextual data from the GUI. The data element remains displayed within the GUI. The methodology 600 concludes at 614.

Referring now to FIG. 7, a methodology 700 executed by a server computing device that facilitates displaying contextual data for a data element is illustrated. The methodology 700 begins at 702, and at 704 the server computing device receives an identifier for a data element from a computing device. At 706, the server computing device retrieves contextual data for the data element based upon the identifier for the data element. At 708, the server computing device transmits the contextual data to the computing device, whereupon the computing device presents the contextual data for the data element within a GUI displayed on a display of the computing device. The methodology 700 concludes at 710.

Figure 8:
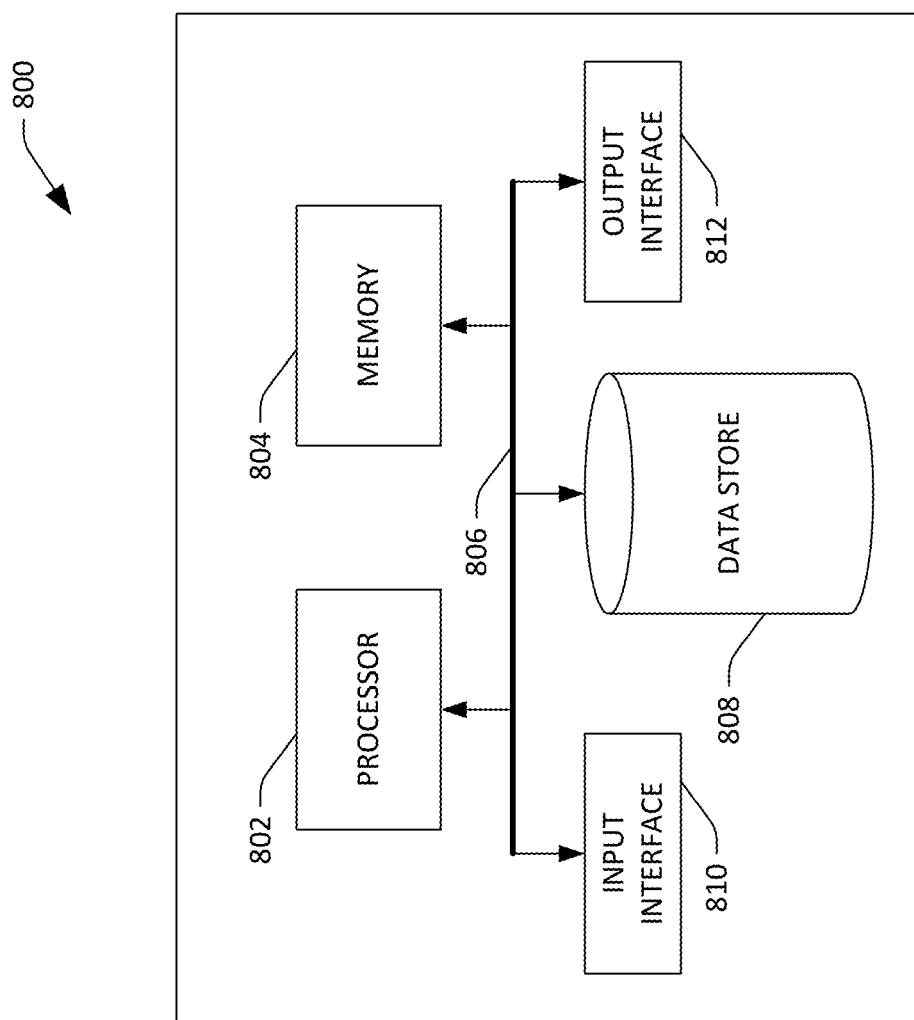
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that facilitates displaying contextual data for a data element within a GUI. By way of another example, the computing device 800 can be used in a system that facilitates displaying contextual data for a data element within a GUI based upon a direction in which a selection article is moved. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store data elements, contextual data for the data elements, clinical data for patients, etc.

The computing device 800 additionally includes a data store 808 that is accessible by the processor 802 by way of the system bus 806. The data store 808 may include executable instructions, data elements, contextual data for the data elements, clinical data for patients, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A computing device comprising:
   a processor;
   a display; and
   memory storing instructions that, when executed by the processor, cause the processor to perform acts comprising:
      displaying a graphical user interface (GUI) of an electronic health records application (EHR) on the display, wherein the GUI comprises clinical data for a patient;
      receiving a first indication that the clinical data has been selected within the GUI by a selection article;
      as the clinical data remains selected within the GUI by the selection article, receiving a second indication that the selection article has been moved in a first direction from amongst a plurality of directions;
      as the clinical data remains selected within the GUI by the selection article and responsive to receiving the second indication that the selection article has been moved in the first direction, updating the GUI to display first contextual data for the clinical data that, prior to receiving the second indication, was not displayed within the GUI, wherein at least a portion of the clinical data is displayed concurrently with the first contextual data for the clinical data within the GUI, wherein the first contextual data for the clinical data is displayed based upon the first direction the selection article was moved;
      responsive to receiving a third indication that the selection article no longer selects the clinical data displayed within the GUI, and without receiving further selection within the GUI by the selection article, removing the first contextual data for the clinical data from the GUI, wherein the clinical data remains displayed within the GUI;
      receiving a fourth indication that the clinical data has been selected within the GUI by the selection article;
      as the clinical data remains selected within the GUI by the selection article, receiving a fifth indication that the selection article has been moved in a second direction from amongst the plurality of directions;
      as the clinical data remains selected within the GUI by the selection article and responsive to receiving the fifth indication that the selection article has been moved in the second direction, updating the GUI to display second contextual data for the clinical data that, prior to receiving the fifth indication, was not displayed within the GUI, wherein at least a portion of the clinical data is displayed concurrently with the second contextual data for the clinical data within the GUI, wherein the second contextual data for the clinical data is displayed based upon the second direction the selection article was moved; and
      responsive to receiving a sixth indication that the selection article no longer selects the clinical data displayed within the GUI, and without receiving further selection within the GUI by the selection article, removing the second contextual data for the clinical data from the GUI, wherein the clinical data remains displayed within the GUI.

2. The computing device of claim 1, wherein the display is a touchscreen, wherein the selection article is a digit of a user of the computing device.

3. The computing device of claim 1, wherein the selection article is a mouse, wherein the mouse is in communication with the computing device.

4. The computing device of claim 1, wherein the computing device is in network communication with a server computing device, the acts further comprising:
   prior to displaying the first contextual data for the clinical data and subsequent to receiving the second indication, transmitting an identifier for the clinical data to the server computing device, wherein the server computing device retrieves the first contextual data for the clinical data based upon the identifier for the clinical data, wherein the server computing device transmits the first contextual data to the computing device; and
   receiving the first contextual data from the server computing device.

5. The computing device of claim 1, wherein the first contextual data for the clinical data is one of:
   an identifier for a user that last modified the clinical data;
   a prior version of the clinical data; or
   a projected future version of the clinical data.

6. The computing device of claim 1, wherein the first indication is received by the computing device at a first time, wherein the second indication is received by the computing device at a second time, wherein displaying the first contextual data for the clinical data occurs when the first time and the second time are within a threshold time range.

7. The computing device of claim 1, wherein the first contextual data for the clinical data is presented as a pane within the GUI, wherein the pane is presented as an overlay to the clinical data, wherein the pane comprises a first portion and a second portion, wherein the first portion of the pane is displayed within the GUI when the selection article is moved to a first point in the first direction, wherein the first portion of the pane and the second portion of the pane are displayed within the GUI when the selection article is moved to a second point in the first direction.

8. The computing device of claim 1, wherein the clinical data is highlighted within the GUI to indicate that the first contextual data for the clinical data and the second contextual data for the clinical data are available.

9. The computing device of claim 1, wherein the plurality of directions comprises the first direction, the second direction, a third direction, and a fourth direction, wherein the first direction is orthogonal to the second direction, wherein the second direction is orthogonal to the third direction, wherein the third direction is orthogonal to the fourth direction, wherein the fourth direction is orthogonal to the first direction.

10. A method executed by a processor of a computing device, the method comprising:
    displaying a graphical user interface (GUI) of an electronic health records application (EHR) on a display of the computing device, wherein the GUI comprises clinical data for a patient;
    receiving a first indication that the clinical data has been selected within the GUI by a selection article;
    as the clinical data remains selected within the GUI by the selection article, receiving a second indication that the selection article has been moved in a first direction from amongst a plurality of directions;
    as the clinical data remains selected within the GUI by the selection article and responsive to receiving the second indication, updating the GUI to display first contextual data for the clinical data that, prior to receiving the second indication, was not displayed within the GUI, wherein at least a portion of the clinical data is displayed concurrently with the first contextual data for the clinical data within the GUI, wherein the first contextual data for the clinical data is displayed based upon the first direction the selection article was moved;
    responsive to receiving a third indication that the selection article no longer selects the clinical data displayed within the GUI, and without receiving further selection within the GUI by the selection article, removing the first contextual data for the clinical data from the GUI, wherein the clinical data remains displayed within GUI;
    receiving a fourth indication that the clinical data has been selected within the GUI by the selection article;
    as the clinical data remains selected within the GUI by the selection article, receiving a fifth indication that the selection article has been moved in a second direction from amongst the plurality of directions;
    as the clinical data remains selected within the GUI by the selection article and responsive to receiving the fifth indication that the selection article has been moved in the second direction, updating the GUI to display second contextual data for the clinical data that, prior to receiving the fifth indication, was not displayed within the GUI, wherein at least a portion of the clinical data is displayed concurrently with the second contextual data for the clinical data within the GUI, wherein the second contextual data for the clinical data is displayed based upon the second direction the selection article was moved; and
    responsive to receiving a sixth indication that the selection article no longer selects the clinical data displayed within the GUI, and without receiving further selection within the GUI by the selection article, removing the second contextual data for the clinical data from the GUI, wherein the clinical data remains displayed within the GUI.

11. The method of claim 10, wherein the first indication is received by the computing device at a first time, wherein the second indication is received by the computing device at a second time, wherein displaying the first contextual data for the clinical data occurs when the first time and the second time are within a threshold time range.

12. The method of claim 10, wherein the display is a touchscreen, wherein the selection article is a digit of a user, wherein the computing device is operated by the user.

13. The method of claim 10, wherein the plurality of directions comprises the first direction, the second direction, a third direction, and a fourth direction, wherein the first direction is orthogonal to the second direction, wherein the second direction is orthogonal to the third direction, wherein the third direction is orthogonal to the fourth direction, wherein the fourth direction is orthogonal to the first direction.

14. A computer-readable storage medium comprising instructions that, when executed by a processor of a computing device, cause the processor to perform acts comprising:
    displaying a graphical user interface (GUI) of an electronic health records application (EHR) on a display of the computing device, wherein the GUI comprises clinical data for a patient;

receiving a first indication that the clinical data has been selected within the GUI by a selection article;

as the clinical data remains selected within the GUI by the selection article, receiving a second indication that the selection article has been moved in a first direction from amongst a plurality of directions;

as the clinical data remains selected within the GUI by the selection article and responsive to receiving the second indication, updating the GUI to display first contextual data for the clinical data that, prior to receiving the second indication, was not displayed within the GUI, wherein the first contextual data for the clinical data is based upon the first direction in which the selection article was moved, wherein at least a portion of the clinical data is displayed concurrently with the first contextual data for the clinical data within the GUI;

responsive to receiving a third indication that the selection article no longer selects the clinical data displayed within the GUI, and without receiving further selection within the GUI by the selection article, removing the first contextual data for the clinical data from the GUI, wherein the clinical data remains displayed within the GUI;

receiving a fourth indication that the clinical data has been selected within the GUI by the selection article;

as the clinical data remains selected within the GUI by the selection article, receiving a fifth indication that the selection article has been moved in a second direction from amongst the plurality of directions;

as the clinical data remains selected within the GUI by the selection article and responsive to receiving the fifth indication that the selection article has been moved in the second direction, updating the GUI to display second contextual data for the clinical data that, prior to receiving the fifth indication, was not displayed within the GUI, wherein at least a portion of the clinical data is displayed concurrently with the second contextual data for the clinical data within the GUI, wherein the second contextual data for the clinical data is displayed based upon the second direction the selection article was moved; and responsive to receiving a sixth indication that the selection article no longer selects the clinical data displayed within the GUI, and without receiving further selection within the GUI by the selection article, removing the second contextual data for the clinical data from the GUI, wherein the clinical data remains displayed within the GUI.

15. The computer-readable storage medium of claim 14, wherein the plurality of directions comprises the first direction, the second direction, a third direction, and a fourth direction, wherein the first direction is orthogonal to the second direction, wherein the second direction is orthogonal to the third direction, wherein the third direction is orthogonal to the fourth direction, wherein the fourth direction is orthogonal to the first direction.

16. The computer-readable storage medium of claim 14, wherein the display is a touchscreen, wherein the selection article is a digit of a user of the computing device.

17. The computer-readable storage medium of claim 14, wherein the first contextual data for the clinical data is one of:
an identifier for a user that last modified the clinical data;
a prior version of the clinical data; or
a projected future version of the clinical data.

18. The computer-readable storage medium of claim 14, wherein the first indication is received by the computing device at a first time, wherein the second indication is received by the computing device at a second time, wherein displaying the first contextual data for the clinical data occurs when the first time and the second time are within a threshold time range.

19. The computer-readable storage medium of claim 14, wherein the clinical data is highlighted within the GUI to indicate that the first contextual data for the clinical data is available.

20. The computer-readable storage medium of claim 14, wherein the selection article is a mouse, wherein the mouse is in communication with the computing device.

* * * * *